United States Patent [19]
Bender

[11] 3,965,888
[45] June 29, 1976

[54] SPECIMEN COLLECTOR AND HOLDER
[75] Inventor: Louis Bender, Scotch Plains, N.J.
[73] Assignee: Brenner and Bender, Inc., Warren, N.J.
[22] Filed: Feb. 12, 1975
[21] Appl. No.: 549,164

[52] U.S. Cl. .............................. 128/2 W; 23/292; 356/244
[51] Int. Cl.² ........................................ A61B 10/00
[58] Field of Search ................. 128/2 W, 2 B, 269; 356/244; 23/292; 73/425

[56] References Cited
UNITED STATES PATENTS

| | | | |
|---|---|---|---|
| 2,415,480 | 2/1947 | Gassert | 356/244 X |
| 2,969,057 | 1/1961 | Simmons | 128/2 W |
| 3,146,163 | 8/1964 | Brewer | 23/292 X |
| 3,551,023 | 12/1970 | Brackett | 356/244 X |
| 3,764,215 | 10/1973 | Wallach | 356/36 |
| 3,774,590 | 11/1973 | McDonald | 128/2 B |
| 3,814,522 | 6/1974 | Clark et al. | 23/292 X |

FOREIGN PATENTS OR APPLICATIONS

| | | | |
|---|---|---|---|
| 1,212,404 | 10/1959 | France | 128/2 W |

*Primary Examiner*—Kyle L. Howell
*Attorney, Agent, or Firm*—St. Onge Mayers Steward & Reens

[57] ABSTRACT

A specimen holder is described for collecting and examining a specimen collected from a body. The holder includes a transparent adhesive coated foldable segment. The adhesive is used to collect the specimen and retain the back-folded segment against a flat transparent portion of the holder. Visual examination of the specimen can then be carried out directly through the transparent holder without transfer of the specimen to glass slides or the like.

8 Claims, 8 Drawing Figures

U.S. Patent   June 29, 1976   3,965,888
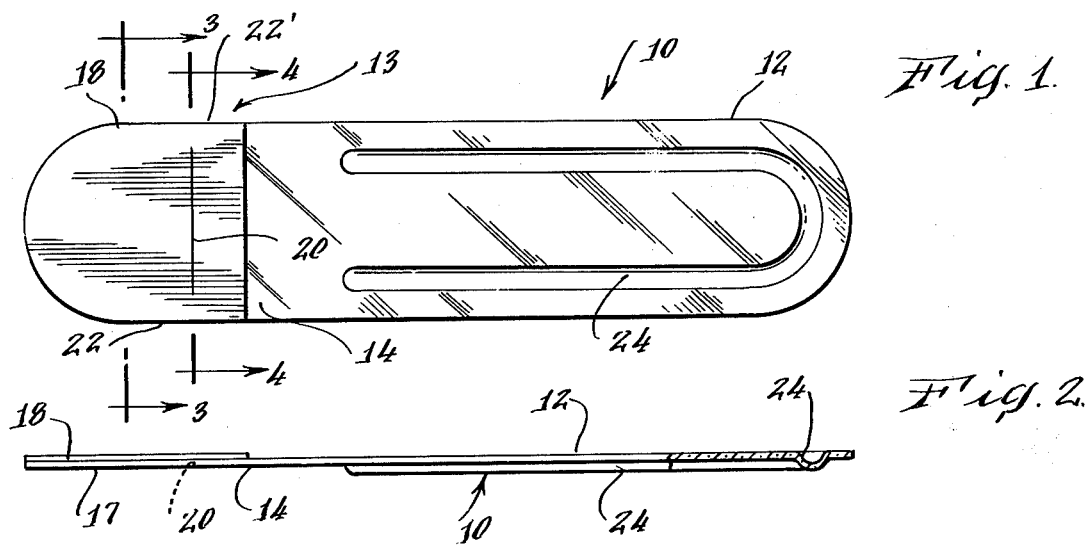
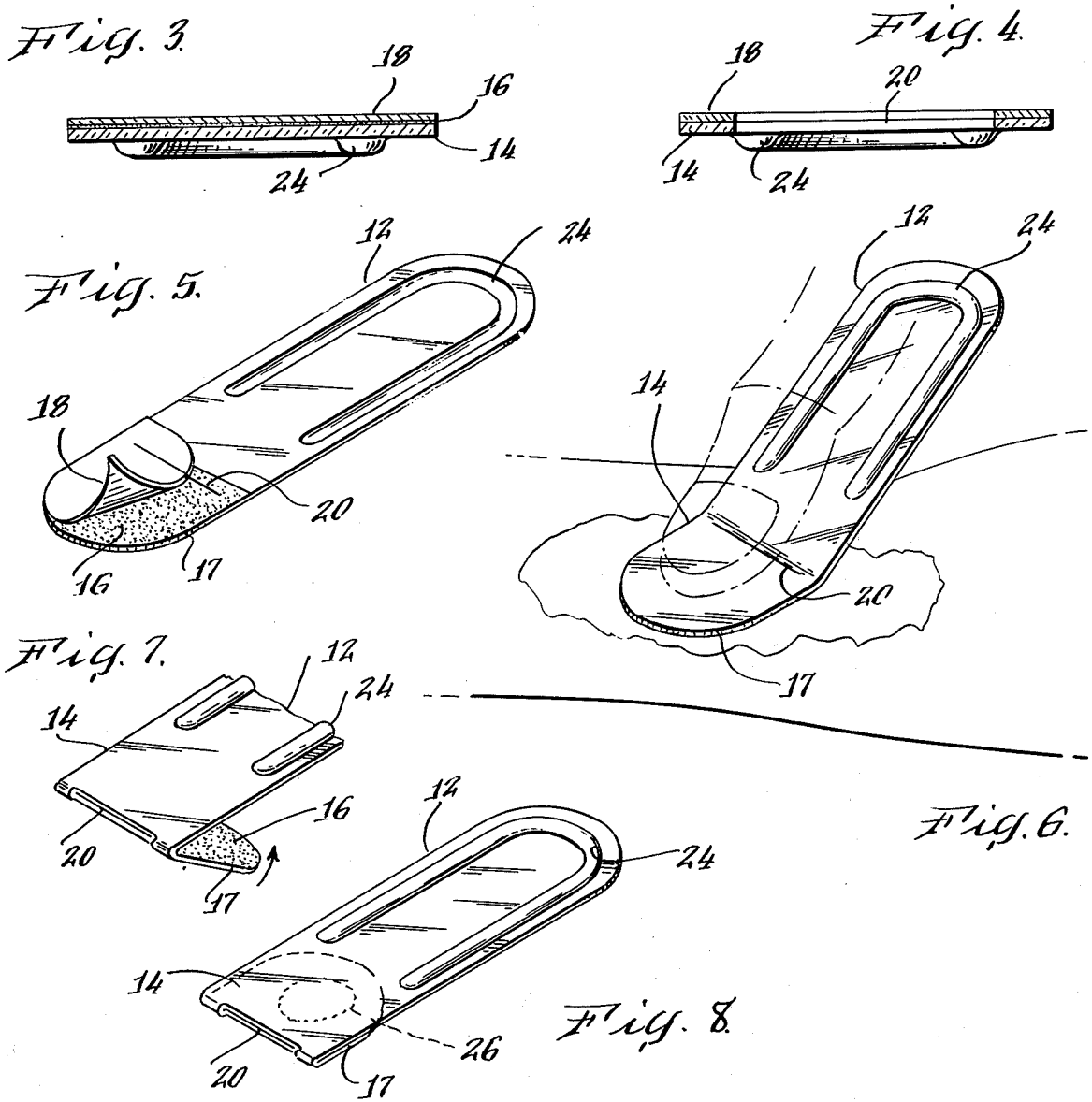

SPECIMEN COLLECTOR AND HOLDER

FIELD OF THE INVENTION

This invention relates to a swab for collecting and holding a specimen for visual examination. More specifically, this invention relates to a swab for holding a specimen obtained for microscope examination.

BACKGROUND OF THE INVENTION

Nematodic swabs for the examination of specimen obtained from a human body have been described in the art. Note, for example, the U.S. patent to Simmons No. 2,969,057. As described in the latter patent, a flexible nematodic swab is formed with a multiple flexible layered structure. One layer is a transparent carrier provided with an adhesive. A protective cover is applied over the adhesive so that it may be preserved until a specimen is to be obtained. When the swab is used, the protective layer is removed and the carrier adhesive applied to the body area from which a specimen is to be obtained.

The adhesive layer is promptly mounted on a microscope glass slide by affixing the adhesive side to the glass for further examination. The carrier tape on which the adhesive is located is formed of a very thin transparent material so that a microscope examination of the specimen adhering to the adhesive below the transparent layer can be made.

In the U.S. Pat. to McDonald No. 3,774,590 a uterine specimen collection device is described formed with a handle portion and a blade with edges and the like. The scraping segment of the device is integrally connected to a main body with a weakened segment adapted to be bent and broken to separate the portions carrying the specimen for analysis.

In the U.S. Pat. to Pickett No. 3,498,860 a structure is described wherein a microscope slide carrying a specimen is analyzed under a microscope after a cover glass is positioned over the slide. A suitable adhesive coating is employed. Many other devices for obtaining specimen are described in U.S. Pat. Nos. to Pell 3,282,114 and Wallach 3,764,215. The swabs described in the prior art generally involve specimen transfer to a suitable glass slide for further processing or medical examination.

SUMMARY OF THE INVENTION

In a specimen holder formed in accordance with the invention, the very swab employed to obtain a specimen from a human body also serves as a microscope slide. In this manner, specimen transfers and the use of glass slides are eliminated while the specimen can be conveniently examined without contamination.

With a specimen holder in accordance with the invention, a swab is formed with a transparent segment carrying an adhesive area to obtain a specimen. The transparent segment is provided with a fold-line located in such manner that the adhesive area may be folded back upon the main body of the swab itself so that the specimen can be examined through the transparent swab.

The swab has shape and rigidity selected to enable singlehanded manipulation of the swab for taking of a specimen. When the specimen sticking to the adhesive area is folded back onto the transparent segment, the specimen is protected against contamination and may be examined through the transparent segment of the swab.

It is, therefore, an object of the invention to provide a specimen holder employable as a swab for taking and examining of a specimen.

These and other objects and advantages of a specimen holder in accordance with the invention can be understood with reference to the following description of a preferred embodiment described in conjunction with the drawings.

BRIEF DESCRIPTION OF DRAWINGS

FIG. 1 is a plan view of a specimen holder in accordance with the invention prior to use;

FIG. 2 is a side view of the specimen holder as shown in FIG. 1;

FIG. 3 is a section view taken along the line 3—3 of the specimen holder shown in FIG. 1;

FIG. 4 is a section view taken along the line 4—4 in FIG. 1;

FIG. 5 is a perspective view of the specimen holder with a protective wrapper partially exposing an adhesive layer;

FIG. 6 is a perspective view of the specimen holder being applied to the surface of a human body for obtaining a specimen;

FIG. 7 is a perspective view of a portion of the specimen holder after taking of a specimen; and FIG. 8 shows the specimen holder after obtaining a specimen and prepared for visual examination.

DETAILED DESCRIPTION OF EMBODIMENT

With reference to FIGS. 1 through 4, a specimen holder 10 in accordance with the invention is illustrated formed of a generally transparent plastic material shaped into a swab having a handle 12 connected to a transparent swab end 14. The transparent swab end 14 is flat and is coated on one side with an adhesive 16 on a foldable portion 17 selected in size to enable the taking of a specimen from the surface of a body. The adhesive coated fold segment 17 is covered by a protective material in the form of a thin sheet 18 which is removable by peeling it away as shown in FIG. 5.

The specimen holder 10 is formed of a generally thin transparent plastic material whose thickness provides sufficient flexibility to enable adhesive collection of specimen from irregular surfaces. On the other hand, the thickness is sufficient to obtain a rigidity for single-handed manipulation. Generally a thickness of about 0.010 inches is sufficient when additional rigidity is achieved with embossments as will be further explained.

A fold-line 20 is located transversely across the main body 12 of the swab. The fold-line 20 is formed with a through-cut which is formed through cover sheet 18 and the swab transparent segment 14. The fold-line cut 20 is sized to terminate short of the side edges 22–22' of segment 14. Hence, the adhesive coated transparent fold segment 17 can be folded back upon the general planar area 14 of the swab 10 as illustrated in FIGS. 7 and 8 to enable visual examination of a specimen through the swab.

Although the score line 20 is shown formed of a cut extending between the sides 22–22' of the swab, other methods of providing a fold-line such as a partially penetrating score line or a plurality of holes extending generally between sides 22–22' of the swab main body can be used.

The handle 12 of the specimen holder 10 is shown provided with an embossment 24 which extends generally longitudinally in a U-shape to enhance the rigidity of the swab for ease of handling. The embossment 24 need not be very large and can be conveniently applied during the formation of the specimen holder 10.

Prior to use of swab 10, the cover sheet 18 is removed as shown in FIG. 5. The adhesive 16 is then applied to a body surface with one finger applying back pressure against the fold segment 17 while the swab is held in one hand as illustrated in FIG. 6. After collection of the specimen 26 by its sticking to the adhesive, the end 17 is bent back upon itself as shown in FIGS. 7 and 8 so that the adhesive segment 17 is located against the transparent flat area 14 of the swab. The specimen 26 can then be examined directly through the transparent swab while being protected against contamination.

Having thus described a specimen holder in accordance with the invention, its advantages can be appreciated. The specimen can be obtained with a holder that is manipulated by one hand. Thereafter, the specimen is preserved against contamination and may be examined without further transfer to glass slides or the like.

What is claimed is:

1. A specimen holder for collecting and enabling examination of specimen comprising
a unitary generally longitudinal swab having an integrally coupled handle segment and a transparent segment provided on one side thereof with an adhesive coated area to retain the specimen when applied thereto, said swab further being provided with a scored fold-line located across the transparent segment to enable the adhesive coated area to be folded back against a transparent portion of the swab for close adherence thereto with specimen protection and for visual examination of the specimen through the transparent segment of the swab.

2. The specimen holder as claimed in claim 1 wherein the transparent segment with the adhesive coated area is located at an end of the longitudinal swab, with the fold-line located to enable the transparent end segment to be folded back onto the swab.

3. The specimen holder as claimed in claim 2 wherein the swab is formed of a generally thin material having a thickness sufficient to enable the adhesion of specimen onto the adhesive area from irregular surfaces while having a rigidity sufficient to enable single-handed manipulation of the swab.

4. The specimen holder as claimed in claim 3 wherein the swab is further provided with a handle segment carrying an embossment located along the swab and terminating before the transparent segment for enhanced rigidity of the swab.

5. The specimen holder as claimed in claim 4 wherein the embossment is U-shaped.

6. The specimen holder as claimed in claim 4 wherein the score line is formed of a transverse oriented cut extending partially across the swab.

7. The specimen holder as claimed in claim 6 wherein the swab is further provided with a removable sheet placed over the adhesive area for its protection prior to application of the swab.

8. The specimen holder as claimed in claim 7 wherein the swab is formed in its entirety of a flat transparent material.

* * * * *